(12) United States Patent
Kinoshita

(10) Patent No.: US 11,371,997 B2
(45) Date of Patent: Jun. 28, 2022

(54) GLYCAN ANALYSIS METHOD, GLYCAN ANALYSIS SYSTEM, PROGRAM FOR GLYCAN ANALYSIS, AND KIT FOR GLYCAN ANALYSIS

(71) Applicant: SHIMADZU CORPORATION, Kyoto (JP)

(72) Inventor: Mitsuhiro Kinoshita, Osaka (JP)

(73) Assignee: SHIMADZU CORPORATION, Kyoto (JP)

( * ) Notice: Subject to any disclaimer, the term of this patent is extended or adjusted under 35 U.S.C. 154(b) by 147 days.

(21) Appl. No.: 16/286,937

(22) Filed: Feb. 27, 2019

(65) Prior Publication Data
US 2019/0265246 A1 Aug. 29, 2019

(30) Foreign Application Priority Data
Feb. 28, 2018 (JP) .............................. JP2018-035083

(51) Int. Cl.
*G01N 33/58* (2006.01)
*G01N 27/447* (2006.01)
(Continued)

(52) U.S. Cl.
CPC ..... *G01N 33/582* (2013.01); *G01N 27/44791* (2013.01); *G16C 20/20* (2019.02);
(Continued)

(58) Field of Classification Search
CPC ........... G01N 33/582; G01N 27/44791; G01N 2550/00; G01N 2570/00; B01L 3/5027; G16C 20/20
See application file for complete search history.

(56) References Cited

U.S. PATENT DOCUMENTS

2004/0094419 A1   5/2004  Ueda et al.
2004/0112751 A1*  6/2004  Han ................. G01N 27/44795
                                                          204/605

FOREIGN PATENT DOCUMENTS

JP   2002-243701 A   8/2002
JP   2009-036577 A   2/2009
(Continued)

OTHER PUBLICATIONS

Taga, Atsushi, et al. "Simultaneous determination of the association constants of oligosaccharides to a lectin by capillary electrophoresis." Journal of Chromatography A 837.1-2 (1999): 221-229. (Year: 1999).*

(Continued)

*Primary Examiner* — Jennifer Wecker
*Assistant Examiner* — Oyeleye Alexander Alabi
(74) *Attorney, Agent, or Firm* — Sughrue Mion, PLLC

(57) ABSTRACT

A sample, which is a mixture of glycans, is fluorescently labeled (S2). The sample is subsequently separated by microchip electrophoresis under a buffer solution with no lectin added as well as under multiple kinds of buffer solutions with different lectins respectively added, and the separated components are fluorescently detected (S3). A high-concentration gel which can produce a molecular-sieving effect is used as the buffer solution. Multiple electropherograms are created from the detection results (S4). A glycan having a lectin specifically attached is delayed during its migration in the buffer solution, so that a peak corresponding to this glycan will effectively disappear. Accordingly, based on the kinds of lectins and the presence/absence of a peak on each of the electropherograms, the structure of each glycan in the sample is estimated and the glycan is identified (S5).

9 Claims, 7 Drawing Sheets

(51) Int. Cl.
  *G16C 20/20* (2019.01)
  *B01L 3/00* (2006.01)
(52) U.S. Cl.
  CPC ........ *B01L 3/5027* (2013.01); *G01N 2550/00* (2013.01); *G01N 2570/00* (2013.01)

(56) References Cited

FOREIGN PATENT DOCUMENTS

| JP | 2009-74811 A | 4/2009 | | |
|---|---|---|---|---|
| JP | 2009-109325 A | 5/2009 | | |
| WO | 02/44708 A1 | 6/2002 | | |
| WO | 2004/036216 A1 | 4/2004 | | |
| WO | WO-2004036216 A1 * | 4/2004 | ......... | G01N 33/5308 |

OTHER PUBLICATIONS

Schoch, Reto B., Arnaud Bertsch, and Philippe Renaud. "pH-controlled diffusion of proteins with different pI values across a nanochannel on a chip." Nano letters 6.3 (2006): 543-547. (Year: 2006).*

Yamamoto, Sachio, Sho Suzuki, and Shigeo Suzuki. "Microchip electrophoresis of oligosaccharides using lectin-immobilized preconcentrator gels fabricated by in situ photopolymerization." Analyst 137.9 (2012): 2211-2217. (Year: 2012).*

Nakajima, Kazuki, et al. "Capillary affinity electrophoresis using lectins for the analysis of milk oligosaccharide structure and its application to bovine colostrum oligosaccharides." Analytical biochemistry 348.1 (2006): 105-114. (Year: 2006).*

Kakehi et al., "Ultra high sensitive analysis of glycans by capillary electrophoresis with fluorometric detection", Rinshou Kagaku (Clinical Chemistry), Japan Society of Clinical Chemistry, 2005, pp. 326-335, vol. 34, No. 4.

Kinoshita et al., "Tousa Kaiseki Ni Okeru Kyapirarii Denki Eidou Ga Hatasu Yakuwari (Role of Capillary Electrophoresis in Carbohydrate Analysis)", Seibutsu Butsuri Kagaku (Biophysical Chemistry), Japanese Electrophoresis Society, 2008, pp. 111-116, vol. 52.

Suzuki et al., "DNA/RNA Bunseki You Maikuro Chippu Denki Eidou Souchi MCE-202, MultiNA—Kaihatsu To Sono Ouyou—(MCE-202 MultiNA: Microchip Electrophoresis System for DNA/RNA Analysis—Development and Application-)", Shimadzu Hyouron (Shimadzu Review), Shimadzu Hyouron Henshu-bu, 2008, pp. 117-122, vol. 64, No. 3/4.

Office Action dated Jun. 22, 2021 issued by the Japanese Patent Office in Japanese Application No. 2018-035083. Translation.

Communication dated Jan. 18, 2022 from the Japanese Patent Office in Application No. 2018-035083.

* cited by examiner

Fig. 4A
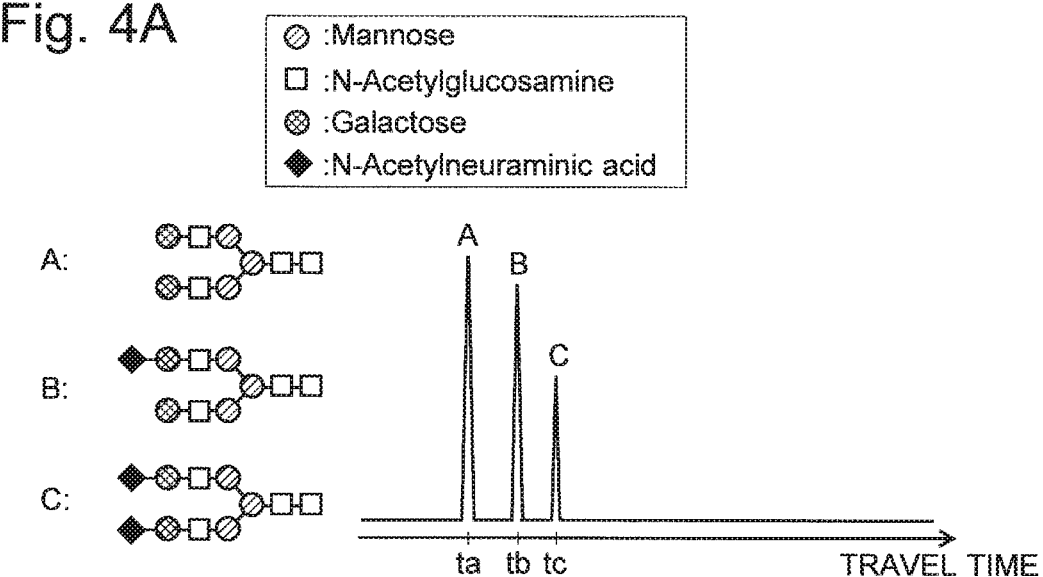
Fig. 4B
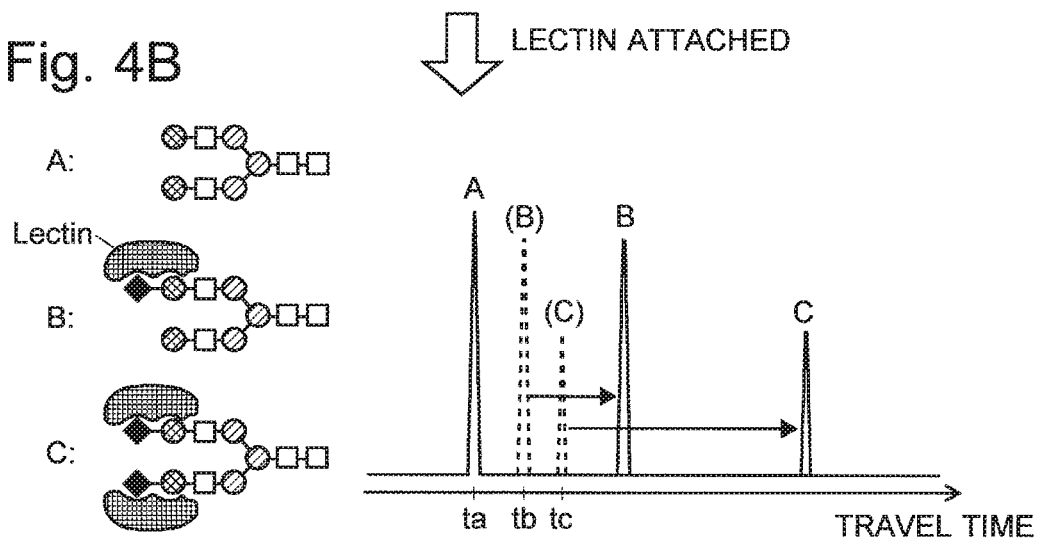
Fig. 5

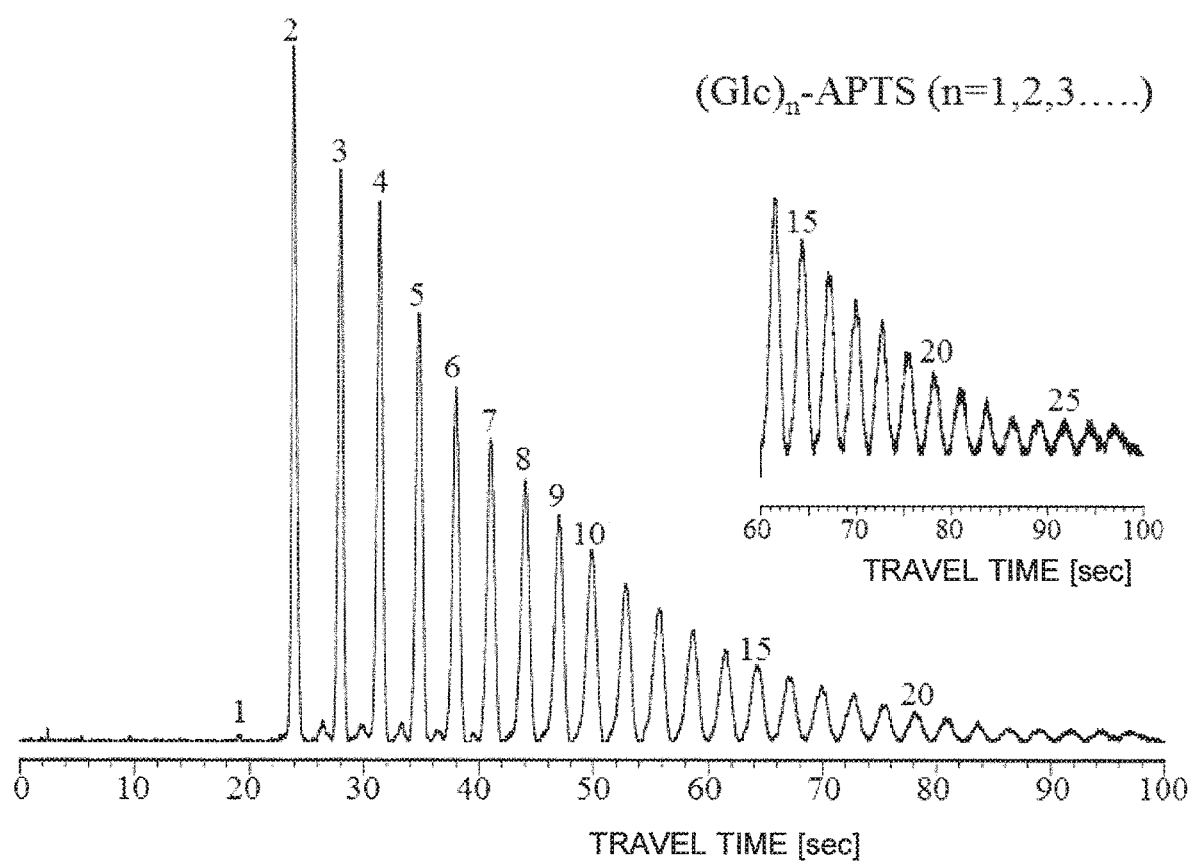

AGP (Asialo), human

ConA (Di-antennary)

DSA (Tri-antennary)

AAL (Fuc α 1-2,3,4,6)

Non Lectin hA1  hA2  hA3  hA4

TRAVEL TIME [sec]

Fibrinogen (Sialo), human

ConA
(Di-antennary)

SSA
(NeuAc α 2-6R)

MAM
(NeuAc α 2-3R)

Non Lectin hF3 hF2 hF1

TRAVEL TIME [sec]

Fig. 9
| PEAK No. | GLYCAN STRUCTURE | LECTIN AFFINITY | | |
|---|---|---|---|---|
| | | ConA | DSA | AAL |
| hA1 | 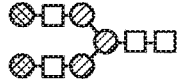 | + | − | − |
| hA2 | 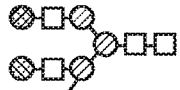 | − | + | − |
| hA3 | 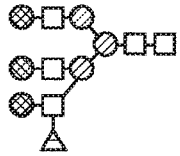 | − | − | + |
| hA4 | 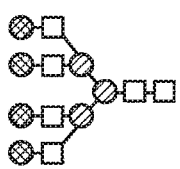 | − | + | − |
Fig. 10
| PEAK No. | GLYCAN STRUCTURE | LECTIN AFFINITY | | |
|---|---|---|---|---|
| | | ConA | SSA | MAM |
| hF1 | 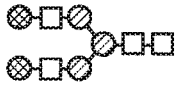 | + | − | − |
| hF2 | 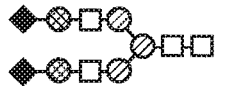 | + | + | − |
| hF3 | 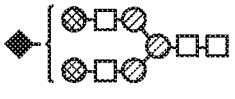 | + | + | − |

GLYCAN ANALYSIS METHOD, GLYCAN ANALYSIS SYSTEM, PROGRAM FOR GLYCAN ANALYSIS, AND KIT FOR GLYCAN ANALYSIS

TECHNICAL FIELD

The present invention relates to a method for analyzing glycans using electrophoresis, as well as a glycan analysis system, a computer program for glycan analysis and a kit for glycan analysis for performing such an analysis.

BACKGROUND ART

There are a large number of proteins and lipids in living organisms. It has been revealed that many of those proteins and lipids cannot sufficiently function when in their original forms yet can exhibit their functions when modified in specific forms. In particular, it has been known that glycoproteins and glycolipids, which contain glycans attached to proteins or lipids, are involved in various kinds of intravital phenomena, such as cellular interaction, signaling, generation and differentiation as well as fertilization and diseases. Such glycoproteins and glycolipids are also collectively called glycoconjugates.

Glycans which modify proteins or lipids rarely has the structure of a straight chain of monosaccharides. In most cases, glycans have a branched structure. Glycans having such a branched structure are extremely diverse in structure. Their structures significantly affect the functions of the proteins and lipids. Accordingly, analysis of glycans is extremely important in various areas, such as physiology, bioscience, medicine and pharmacy. Meanwhile, analysis of glycan is more difficult than that of proteins or similar substances due to their structural diversity as well as their difficulty in high-volume synthesis.

With the recent and rapid advancement of mass spectrometric techniques, mass spectrometry has also been increasingly applied in the structural analysis of glycans. In particular, mass spectrometric methods called tandem mass spectrometry, MS$^n$ mass spectrometry or the like have been used. However, an analysis of glycans with a high level of sensitivity and accuracy using a mass spectrometric method requires a considerably expensive device. Such an analytical technique cannot be considered as a simple and convenient solution.

A simple and convenient method for glycan analysis has been conventionally known, in which glycans are fluorescently labeled and subjected to an analysis using a device in which a capillary electrophoresis (which is hereinafter abbreviated as "CE") method is coupled with a fluorescence detection method (for example, see Patent Literature 1 or 2). In the CE method, the separation performance changes depending on the separation conditions, such as the selection of the separation mode, kind of buffer solution, pH, presence or absence of an additive, and kind of additive. However, when the sample to be analyzed is a glycan mixture containing multiple kinds of glycans mixed together, it is difficult to optimize the separation conditions for all glycans. Therefore, in some cases, the different kinds of glycans cannot be sufficiently separated from each other. To address this problem, the present inventors have proposed a method named the "capillary affinity electrophoresis" (which is hereinafter abbreviated as 'CAE') method in Non-Patent Literature 1 or 2.

In the CAE method, a mixture of fluorescently-labeled glycans is made to electrophoretically migrate in a buffer solution containing a carbohydrate-binding protein (lectin) having a known carbohydrate-binding specificity. The Lectin binds to a specific monosaccharide or oligosaccharide structure in glycans. Accordingly, a glycan which has that specific structure increases in its apparent mass by an amount corresponding to the attached lectin, while a glycan which does not have the specific structure shows no change in its apparent mass. A glycan whose apparent mass has been larger requires a correspondingly longer time for migration. Accordingly, the migration time varies according to the difference in affinity with lectin. This phenomenon can be used to improve the performance for the separation of glycans.

CITATION LIST

Patent Literature

Patent Literature 1: JP 2009-36577 A
Patent Literature 2: JP 2009-109325 A

Non-Patent Literature

Non-Patent Literature 1: Kakehi, Matsuno and Kinoshita, "Ultra high sensitive analysis of glycans by capillary electrophoresis with fluorometric detection", *Rinshou Kagaku* (*Clinical Chemistry*), Japan Society of Clinical Chemistry, Vol. 34, No. 4, 2005, pp. 326-335

Non-Patent Literature 2: Kinoshita and Kakehi, "Tousa Kaiseki Ni Okeru Kyapirarii Denki Eidou Ga Hatasu Yakuwari (Role of Capillary Electrophoresis in Carbohydrate Analysis)", *Seibutsu Butsuri Kagaku* (*Biophysical Chemistry*), Japanese Electrophoresis Society, Vol. 52, 2008, pp. 111-116

Non-Patent Literature 3: Suzuki and twelve other authors, "DNA/RNA Bunseki You Maikuro Chippu Denki Eidou Souchi MCE-202, MultiNA—Kaihatsu To Sono Ouyou—(MCE-202 MultiNA: Microchip Electrophoresis System for DNA/RNA Analysis—Development and Application—)", Shimadzu Hyouron (Shimadzu Review), Shimadzu Hyouron Henshu-bu, Vol. 64, No. 3/4, 2008, pp. 117-122

SUMMARY OF INVENTION

Technical Problem

A problem of the glycan analysis by the CAE method is that its throughput is low since the method does not allow the washing of the capillary tube, injection of the buffer solution, injection of the sample, execution of electrophoresis as well as other related tasks and operations to be performed in parallel. The CAE method requires a measurement to be performed for the same sample a plurality of times (at least two times, and normally three or more times) in order to identify glycans. Depending on the separation conditions, the CAE method requires several minutes or tens of minutes for each measurement. Furthermore, additional tasks which must be performed for each measurement, such as the washing of the capillary tube and the filling of the tube with the buffer solution, also require a considerable amount of time. Therefore, the entire measurement for one sample normally requires a few hours. Thus, a technique by which a number of samples can be more efficiently analyzed has been requested.

Additionally, in order to increase the number of kinds of glycans that can be identified by the CAE method, it is necessary to perform a measurement using multiple kinds of lectins which differ from each other in carbohydrate-binding specificity. However, experimental tests by the present inventors have demonstrated that the kinds of lectins which are practically available in the CAE method are considerably limited. Its primarily reason is that some kinds of lectins cause a change in the migration time of a glycan for which those lectins should not have any specificity (and should not bind to), i.e. for which no change in the migration time should occur. In such a case, it is impossible to correctly identify the glycan based on its peak position. As a result of such reasons, the kinds of lectins which can be used in the conventional CAE method have been limited, and therefore, the kinds of glycans which can be correctly identified have also been considerably limited.

The present invention has been developed to solve such problems. Its objective is to provide a glycan analysis method which allows for the use of an increased number of kinds of lectins for glycan analysis, and thereby enables the separation and identification of glycans which cannot be properly separated by conventional methods, as well as to provide a glycan analysis system, program for glycan analysis and kit for glycan analysis for carrying out such a method.

Solution to Problem

A glycan analysis method according to the present invention developed for solving the previously described problems includes:

a) a fluorescent-labeling step in which a glycan in a sample is fluorescently labeled;

b) a measurement step in which a sample containing a fluorescently-labeled glycan is separated by a microchip electrophoretic method using at least two kinds of buffer solutions for separation selected from a simple buffer solution with no lectin added and a plurality of kinds of lectin-added buffer solutions each of which contains a different kind of lectin added to the simple buffer solution, and the sample is fluorescently detected; and c) an identification step in which the glycan in the sample is identified by comparing a plurality of electropherograms obtained by a measurement using the at least two kinds of different buffer solutions for separation.

A glycan analysis system according to the present invention developed for solving the previously described problems is a system to be used for the previously described glycan analysis method according to the present invention, the system including:

a) a measurement unit including a microchip electrophoresis section for separating components in a sample and a detection section for fluorescently detecting the components separated by the microchip electrophoresis section;

b) a glycan identification database recording, for known kinds of glycans, information concerning a plurality of electropherograms to be obtained by a measurement using at least two kinds of different buffer solutions for separation selected from a simple buffer solution with no lectin added and a plurality of kinds of lectin-added buffer solutions each of which contains a different kind of lectin added to the simple buffer solution, or information concerning a peak to be observed on the plurality of electropherograms;

c) a peak detector configured to detect a peak on electropherograms individually obtained by a measurement performed on a sample containing an unknown fluorescently-labeled glycan using the measurement unit under each of the at least two kinds of buffer solutions for separation; and d) an identification processor configured to identify the glycan in the sample based on a result of a peak detection by the peak detector and the information recorded in the glycan identification database.

A program for glycan analysis according to the present invention developed for solving the previously described problems is a program to be installed on a computer to carry out the glycan analysis method according to the present invention, the program configured to make the computer function as:

a) a measurement-controlling functional section configured to control an operation of a measurement unit including a microchip electrophoresis section and a detection section, so as to separate a sample containing a fluorescently-labeled glycan by a microchip electrophoretic method using at least two kinds of buffer solutions for separation selected from a simple buffer solution with no lectin added and a plurality of kinds of lectin-added buffer solutions respectively prepared by adding a plurality of kinds of lectins to the simple buffer solution, and to fluorescently detect the sample; and b) an identification processing functional section configured to create a plurality of electropherograms each of which is based on data obtained by a measurement using one of the at least two kinds of different buffer solutions for separation under a control of the measurement-controlling functional section, and to identify the glycan in the sample by comparing the plurality of electropherograms.

A kit for glycan analysis according to the present invention developed for solving the previously described problems is a kit for glycan analysis to be used for carrying out the glycan analysis method according to the present invention, the kit including a plurality of kinds of lectins to be added to prepare buffer solutions for separation.

This kit for glycan analysis may additionally include a buffer solution with no lectin added, or reagents for preparing this buffer solution.

The glycan analysis method according to the present invention is similar to the conventional CAE method in that the carbohydrate-binding specificity of lectins is used to improve the separability of glycans. A difference exists in that a microchip electrophoresis (which is hereinafter abbreviated as "ME") method is used in place of the CE method for the separation of a plurality of kinds of glycans contained in a sample. The ME method is a technique which uses a microchip for separating components in a sample. A microchip is a substrate made of glass, plastic or quartz on which a micro-sized channel measuring tens to hundreds of micrometers in both width and depth is formed. Microchips are commonly used for the separation of DNA RNA or similar purposes. The ME method requires a shorter period of time for the measurement than the CE method since the separation channel is dramatically shorter than in the CE method. The task of washing the channel and filling the channel with a buffer solution also requires a shorter period of time. Therefore, even if a measurement for one sample is performed a plurality of times under different kinds of buffer solutions, the total amount of measurement time will be dramatically shorter than in the case of a measurement by the CAE method. An example of a device available for a measurement by the ME method is the microchip electrophoresis device MCE-202 manufactured by Shimadzu Corporation, which is described in Non-Patent Literature 3.

As compared to the commonly used CE methods, the ME method allows for the use of a higher amount of pressure to inject a buffer solution into the channel in the microchip. Accordingly, a separating gel having a high concentration that can produce a molecular-sieving effect can be used. For example, such a separating gel can be prepared by mixing an appropriate kind of neutral polymer (e.g. hydroxypropyl methylcellulose, polyethylene glycol or hydroxypropyl cellulose) into a common liquid buffer at an appropriate concentration. The use of such a separating gel which produces a molecular-sieving effect as the buffer solution in the ME method has the following advantage:

As noted earlier, the kinds of lectins which can be used in the conventional CAE method are limited. The present inventors have repeated various experiments and consequently revealed that a cause of the limitation is as follows: In the previously described CAE method, since it is difficult to introduce a high-concentration gel into a capillary tube having an extremely small diameter, a buffer solution which effectively produces no molecular-sieving effect is inevitably used for separating the fluorescently-labeled glycans. In the CE method, glycans can be separated to a certain extent even when there is effectively no molecular-sieving effect, since the CE method allows for the creation of a stronger electric field in the buffer solution than the ME method. However, in the case of the CAE method, when there is no molecular-sieving effect, a phenomenon may occur in which a lectin itself or a complex of the lectin and a glycan also migrates toward the anode or cathode due to the effect of the electric field, depending on the isoelectric point of the lectin which is a type of protein. In other words, the lectin cannot function as a pseudo-stationary phase. This may result in a decrease in the difference in the time of the arrival at the detector between a glycan with a lectin attached and a glycan with no lectin attached, or the time difference may become larger than the amount which is due to the interaction between the lectin and the buffer solution, with the result that the peaks of the glycans overlap each other on the electropherogram. A preferable method for avoiding this situation to use a lectin having an isoelectric point within a range of approximately ±1 from the pH value of the buffer solution for electrophoresis. However, there is only a small number of lectins having such properties.

By comparison, in the ME method, a separating gel having a sufficient level of concentration for producing the molecular-sieving effect can be used as the buffer solution. Under the condition that the molecular-sieving effect is thus sufficiently exhibited, lectins apparently do not migrate within the channel and can function as the pseudo-stationary phase, regardless of the kinds of lectins. Therefore, the migration speed of a glycan with a lectin attached becomes dramatically lower than that of a glycan with no lectin attached, regardless of the kind of lectin, i.e. without depending on the isoelectric point or molecular weight of the lectin. Accordingly, the separation of different kinds of glycans according to the carbohydrate-binding specificity of lectins can be sufficiently achieved with a considerable number of kinds of lectins, inclusive of those which have been unavailable for the CAE method. Consequently, a significant number of kinds of glycans can be identified, inclusive of those which have conventionally been difficult or impossible to identify.

As a specific example, *Sambucus sieboldiana* Agglutinin (SSA), which exhibits a specificity for N-acetylneuraminic acid (NeuAc), has an isoelectric potential (PI) of 5.4-5.8, while *Maackia amurensis* (MAM), which also exhibits a specificity for N-acetylneuraminic acid, has a PI of 4.7. These lectins cannot be used in common CAE methods. By comparison, the present invention does not have any problem with the use of those lectins and enables the separation of glycans using the N-acetylneuraminic-acid-specificity of those lectins.

Thus, as a preferable mode of the glycan analysis method according to the present invention, the simple buffer solution may be a separating gel having a concentration which produces a molecular-sieving effect.

In other words, the simple buffer solution may be a separating gel having a concentration which makes the electrophoretic migration of proteins, such as lectins, effectively ignorable.

The electrophoretic migration of proteins in a buffer solution does not occur if there is no interaction between the buffer solution and the proteins. Accordingly, the simple buffer solution may be a buffer solution which effectively has no interaction with proteins.

The addition of a lectin may possibly change the pH of the buffer solution and unfavorably cause a change in the separation characteristics in the electrophoresis depending on the presence or absence of a lectin or the kind of lectin added. Such a situation causes a problem with the identification of glycans since it is no longer guaranteed that a peak located at the same point in migration time on a plurality of electropherograms always originates from the same glycan. Accordingly, in the glycan analysis method according to the present invention, the simple buffer solution should preferably be a buffer solution which undergoes no substantial change in pH due to the addition of a lectin.

In order to identify multiple kinds of glycans by the glycan analysis method according to the present invention, the level of glycan separation performance under the conditions that no lectin is added must be high to a certain extent. Accordingly, in the glycan analysis method according to the present invention, the separation conditions in the microchip electrophoresis method including the kind of simple buffer solution should preferably be such conditions under which glycans having different degrees of polymerization ranging from monosaccharide to icosasaccharide can be separated from each other in a measurement of an isomalto-oligosaccharide mixture.

The presence of a lectin which does not bind to a specific kind of glycan, i.e. the presence of a lectin which is non-specific to this glycan, may possibly affect the migration time of this glycan and cause a problem with the identification of the glycan. Accordingly, in the glycan analysis method according to the present invention, the separation conditions in the microchip electrophoresis method including the kind of simple buffer solution may preferably be such conditions under which addition or non-addition of a lectin to the simple buffer solution causes no change in migration time of a glycan for which the lectin has no specificity.

Experiments by the present inventors have confirmed that SSA (*Sambucus sieboldiana* Agglutinin), MAM (*Maackia amurensis*). DSA (*Datura stramonium* Agglutinin) and other kinds of lectins which have not been available in the conventional CAE method can be used in the glycan analysis method according to the present invention. The use of at least one of those lectins which have not been available in the conventional CAE method enables high-accuracy identification of a glycan which has conventionally been impossible to identify or has been identified with an insufficient level of accuracy.

Advantageous Effects of Invention

As compared to the conventional CAE method, the present invention can shorten the period of time required for a measurement of one sample which, for example, is a mixture of glycans, and thereby improve the throughput of the analyzing task. The present invention also enables the identification of a significant number of kinds of glycans, inclusive of those which could not be identified by the conventional CAE method. The accuracy of the identification of glycans can also be improved.

BRIEF DESCRIPTION OF DRAWINGS

FIGS. 4A and 4B are diagrams illustrating the principle of the glycan separation using a lectin in the glycan analysis method according to the present invention.

FIG. 5 is one example of the glycan identification database in the glycan analysis system according to the embodiment.

FIG. 6 is a measured example of an electropherogram obtained by a measurement of an isomalto-oligosaccharide mixture.

FIG. 9 shows the result of a prediction in which the glycans corresponding to the peaks in the asialoglycan mixture derived from human AGP were predicted from the result shown in FIGS. 7A-7D.

FIG. 10 shows the result of a prediction in which the glycans corresponding to the peaks in the sialoglycan derived from human fibrinogen were predicted from the result shown in FIGS. 8A-8D.

DESCRIPTION OF EMBODIMENTS

Figure 1:
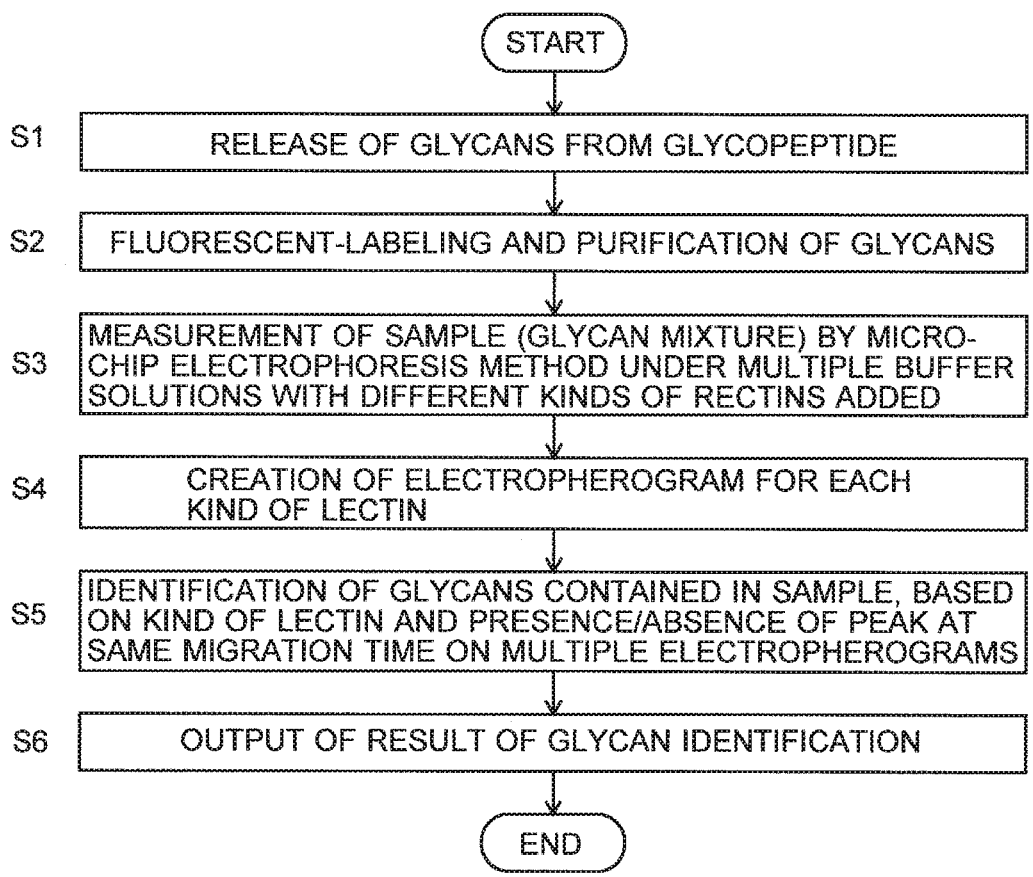
FIG. 1 is a flowchart showing the working and processing steps in one embodiment of the glycan analysis method according to the present invention.

One embodiment of the glycan analysis method according to the present invention as well as the glycan analysis system, program for glycan analysis and kit for glycan analysis for carrying out the same method is hereinafter described with reference to the attached drawings.

In advance of the description of the glycan analysis method according to the present embodiment, the principle of the method for improving the accuracy of the glycan separation using a lectin is described with reference to FIGS. 4A and 4B.

[Principle of Glycan Separation Using Lectin]

It is hereinafter assumed that the sample is a glycan mixture in which three kinds of glycans A, B and C having two-branched structures as shown in FIGS. 4A and 4B are mixed together. If the glycans contained in this sample are each fluorescently labeled and subjected to a measurement by a CE method using a predetermined buffer solution, an electropherogram as shown in FIG. 4A will be obtained since a glycan having a larger mass-to-charge ratio requires a longer travel time (migration time). Specifically, three peaks which respectively correspond to the three glycans A, B and C are observed at travel times ta, tb and tc in ascending order of relative mass-to-charge ratio. Although the three peaks in FIG. 4A are completely separated from each other, those peaks are still considerably close to each other. Accordingly, depending on the separation conditions (or on the kinds of glycans), the separation of those peaks may become insufficient, and the neighboring peaks may overlap each other.

Now, consider the case where the same sample is subjected to a measurement by the CE method using a buffer solution to which a lectin that binds to a specific structure in a glycan with a high degree of affinity (i.e. a lectin having a carbohydrate-binding specificity) is added. In the present example, a lectin having a high degree of affinity with the linkage site of N-acetylneuraminic acid and galactose is used. Therefore, as shown in FIG. 4B, one lectin binds to glycan B, while two lectins bind to glycan C. No lectin binds to glycan A, since there is no N-acetylneuraminic acid in glycan A. The apparent mass of each of the glycans B and C increases by an amount corresponding to the attached lectin. Therefore, in the electropherogram obtained in the present case, the position of the peak of glycan A remains unchanged, whereas those of the peaks of glycans B and C are each significantly delayed.

Accordingly, by comparing the electropherogram shown in FIG. 4A and the one shown in FIG. 4B, it is possible to estimate, for example, that a glycan showing no change in the peak position under the presence of the lectin is a glycan which has no N-acetylneuraminic acid. As for the two glycans whose peaks at positions tb and tc disappear (or whose travel times are delayed) under the presence of the lectin, it is possible to estimate that they are either glycan B or C which has at least one N-acetylneuraminic acid. As shown in FIG. 4A, if the peaks corresponding to glycans B and C have been sufficiently separated under the condition with no lectin present, it is possible to estimate that the one having the shorter travel time is glycan B which has one N-acetylneuraminic acid, while the one having the longer travel time is glycan C which has two N-acetylneuraminic acids.

The previous description is concerned with the case of using a lectin which has a binding-specificity for the linkage site of N-acetylneuraminic acid and galactose. There are many kinds of lectins which vary in carbohydrate-binding specificity, such as mannose-specific lectins (e.g. ConA, or concanavalin A), fucose-specific lectins (e.g. AAL (*Aleuria aurantia* lectin) and UEA-I (*Ulex europaeus* agglutinin I)). If a measurement for a glycan is performed by the CE method using various kinds of lectins, a peak which is expected to be observed at a specific travel time in the obtained electropherogram will appear or disappear depending on the structure of the glycan. Based on the relationship between the kind of used lectin and the appearance or disappearance of a peak, the structure of the glycan can be predicted, i.e. the glycan can be identified.

The separation of glycans based on such a principle is also carried out in the CAE method described in Non-Patent Literature 1 or 2. However, as already explained, the kinds of lectins which can be used in the CAE method are considerably limited, and therefore, the kinds of glycans which can be identified are also limited. By comparison, the glycan analysis method according to the present invention allows for the use of an increased number of kinds of lectins and thereby enables the identification of multiple kinds of glycans with a high level of throughput, as will be hereinafter described.

[Separation Conditions in ME Method]

Unlike the conventional CAE method which employs the CE method for the separation of glycans, the glycan analysis method according to the present invention employs a microchip electrophoresis (ME) method for the separation of glycans. A device for carrying out the ME method will be described later in detail. In the ME method, since a separation channel which is not more than several ten millimeters long is used for the separation of components in a sample, the period of time required for a measurement of a sample one time is dramatically shorter than in the CE method. The use of the shorter channel also means a shorter period of time required for the task of washing the channel and filling the channel with a buffer solution. This improves the throughput of the measurement and contributes to a quicker analysis of glycans.

In the CE method, it is difficult to use a high-concentration gel having a low level of fluidity as the buffer solution. In the ME method, even if the buffer solution is a high-concentration gel, the channel can be filled with the buffer solution within a short period of time due to the shortness of the channel as well as due to the presence of four open ends in the channel which allows the buffer solution to be injected from one open end into the channel while three other ends are in the open state. Thus, a high-concentration gel which can produce a sufficient molecular-sieving effect can be used as the buffer solution. Experimental studies by the present inventors have demonstrated that using a buffer solution which cannot produce a sufficient molecular-sieving effect tends to cause the lectin, which is a type of protein, to migrate toward the anode or cathode due to the effect of the electric field. In order to avoid this problem, the lectin must have an isoelectric point within a range of approximately ±1 from the pH value of the buffer solution. However, there is only a small number of lectins having such properties.

On the other hand, the use of a separating gel having a high concentration that can produce a sufficient molecular-sieving effect allows for the use of various lectins regardless of their isoelectric point and other properties. For this reason, the glycan analysis method according to the present invention uses a separating gel having a high concentration that can produce the molecular-sieving effect as the buffer solution in the ME method. The "concentration that can sufficiently produce the molecular-sieving effect" can be rephrased as a concentration at which the electrophoretic migration of proteins inclusive of lectins will be effectively ignorable. Such a high-concentration gel can be prepared by mixing a neutral polymer (e.g. hydroxypropyl methylcellulose, polyethylene glycol or hydroxypropyl cellulose) into a common liquid buffer at an appropriate concentration.

The component-separating characteristics in the ME method are related to not only the kind of buffer solution but also the migration voltage. If an attempt to separate glycans in a glycan mixture under a buffer solution with no lectin added cannot result in a sufficient separation of the individual glycans to a certain extent, it will be difficult in the first place to determine whether or not a peak has disappeared under a buffer solution with a lectin added. Accordingly, the separation conditions including the migration voltage have been determined so that peaks originating from glycans having different degrees of polymerization ranging from monosaccharide to at least icosasaccharide can be separated from each other in a measurement of an isomalto-oligosaccharide mixture under the buffer solution with no lectin added.

Specific Example of Separation Conditions, and Measured Examples

A microchip electrophoresis device MCE-202, manufactured by Shimadzu Corporation, was used in an actual measurement. A separating gel can be prepared by adding a neutral polymer to a common buffer solution. The present inventors experimentally tested several kinds of polymers at several concentrations and decided to use an 80 mM tris acetic acid buffer (pH 7.5) containing hydroxypropyl methylcellulose (HPMC) at a concentration of 2%. As for the voltages applied for sample introduction or electrophoretic migration, the present inventors experimentally tested voltage programs installed in the built-in software of the used microchip electrophoresis device, and selected the most suitable one.

Under the previously described conditions, an experiment was performed to verify that the glucose in the isomalto-oligosaccharide mixture, which is an α1-6-linked oligomer of glucose, can be separated. FIG. 6 is an electropherogram obtained by a measurement of APTS-labeled isomalto-oligosaccharide mixture. The numbers shown above the individual peaks each denote the degree of polymerization. As shown in FIG. 6, isomaltose, which is a disaccharide, was observed after 24 seconds from the beginning of the measurement followed by a series of sufficiently separated peaks arranged in ascending order of the degree of polymerization up to icosapentasaccharide. An investigation of the quantitative limit and linearity using isomaltohexaose ($Glu_6$-APTS) demonstrated that the lower quantitative limit was equal to or less than 8 pmol/mL, and the linearity was satisfactorily high, with the correlation coefficient being R=0.999 within a concentration range from the lower quantitative limit to approximately 1000 pmol/mL.

Thus, it was confirmed that a sufficient level of separating power and sensitivity for glycan analysis can be achieved by appropriately setting the separation conditions using a commonly available microchip electrophoresis device.

In order to test the effectiveness of the previously described method of glycan identification by the addition of a lectin in a microchip electrophoresis device having such a high separating power, a measurement was performed for two samples.

The first sample was asialoglycan (a glycan having N-acetylneuraminic acid) derived from al-acid glycoprotein (AGP) derived from human serum. Electropherograms for this sample was obtained by a measurement with no lectin added as well as with three lectins individually added. The measured results were as shown in FIGS. 7A-7D. Human AGP includes, as its main N-linked glycan backbone, a complex di-antennary glycan, a complex tri-antennary glycan and its fucosylated glycan (fucose-modified glycan), as well as a complex tetra-antennary glycan and its fucosylated glycan. Four peaks originating from these glycans are observed on an electropherogram obtained under the no-lectin buffer solution with no lectin added (FIG. 7D).

Figure 7A:
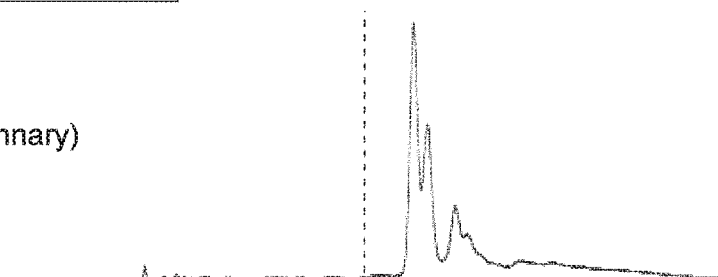
FIGS. 7A-7D each show a measured example of an electropherogram obtained by a measurement of a glycan mixture (asialoglycan derived from human AGP) using a buffer solution to which a lectin was added.
Figure 7B:
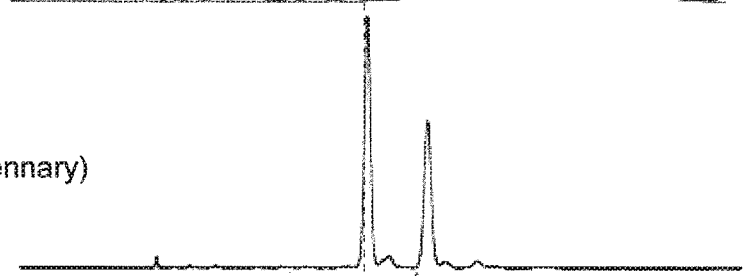
Figure 7C:
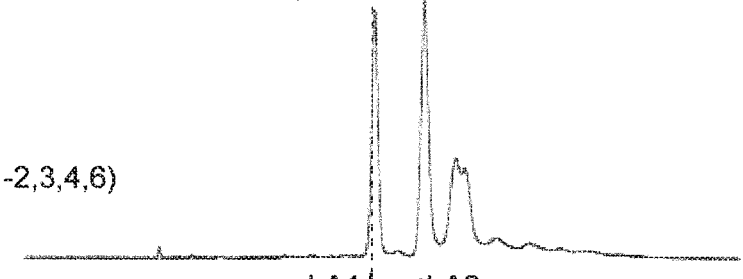
Figure 7D:

In the case of using ConA, which is a lectin that strongly binds to the complex di-antennary glycan and high-mannose glycan, the peak hA1 completely disappears while the other peaks remain unchanged, as shown in FIG. 7A. In the case of using DSA, which is a lectin that binds to the complex tri-antennary glycan and complex tetra-antennary glycan modified with neither fucose nor N-acetylneuraminic acid, the peaks hA2 and hA4 completely disappear, as shown in FIG. 7B. In the case of using AAL, which is a lectin that binds to the α-linked fucose residue, the peak hA3 completely disappears while the other peaks remain unchanged, as shown in FIG. 7C. From the results obtained for the individual lectins, each peak in the asialoglycan mixture derived from human AGP can be assigned as shown in FIG. 9.

Figures 8A, 8B, 8C, 8D:
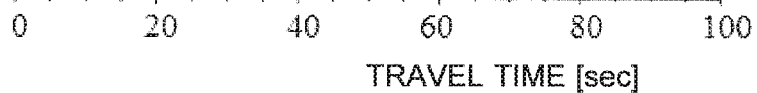
FIGS. 8A-8D each show a measured example of an electropherogram obtained by a measurement of a glycan mixture (sialoglycan derived from human fibrinogen) using a buffer solution to which a lectin was added.

The second sample was a sialoglycan (a glycan which has no N-acetylneuraminic acid) derived from human fibrinogen. Electropherograms for this sample was obtained by a measurement with no lectin added as well as with three lectins individually added. The measured results were as shown in FIGS. 8A-8D. It is commonly known that human fibrinogen includes only the complex di-antennary glycan as its complex glycan backbone. Three peaks originating from this glycan appear on an electropherogram obtained under the no-lectin buffer solution (FIG. 8D).

In the case of using ConA as the lectin, all peaks completely disappear, as shown in FIG. 8A. In the case of using SSA, which is a lectin that binds to an N-acetylneuraminic acid residue which is α2-6-linked to the non-reducing terminal of a glycan, the peaks hF2 and hF3 completely disappear while the peak hF1 remains unchanged, as shown in FIG. 8B. In the case of using MAM, which is a lectin that binds to an N-acetylneuraminic acid residue which is α2-3-linked to the non-reducing terminal of a glycan, all peaks remain unchanged, as shown in FIG. 8C. From the results obtained for the individual lectins, each peak in the sialoglycan mixture derived from human fibrinogen can be assigned as shown in FIG. 10.

As can be seen in FIGS. 7A-7D and FIGS. 8A-8D, whether or not a lectin is added barely affects the position of the peak of the same glycan. This means that the lectin, which is a type of protein, apparently remains at the predetermined position in the channel and functions as the pseudo-stationary phase. Therefore, there is effectively no interaction between the buffer solution and the lectin. Changing the kind of added lectin also barely affects the position of the peak of the same glycan. This fact demonstrates that the addition of lectins effectively causes no change in the pH of the buffer solution.

Thus, it has been experimentally confirmed that the application of the previously described technique of selectively separating glycans using the carbohydrate-binding specificity of lectins in the ME method makes it possible to sufficiently distinguish between glycans having different basic backbones and terminal modifications in a glycan mixture, and thereby identify the glycans. In particular, SSA and MAM are kinds of lectins which cannot be used in the conventional CAE method. Thus, the glycan analysis method according to the present invention allows for the use of lectins which have been unavailable in the conventional CAE method, which leads to a dramatic increase in the number of kinds (structures) of glycans that can be identified, as will be described later.

[Configuration of Glycan Analysis System]

Figure 2:
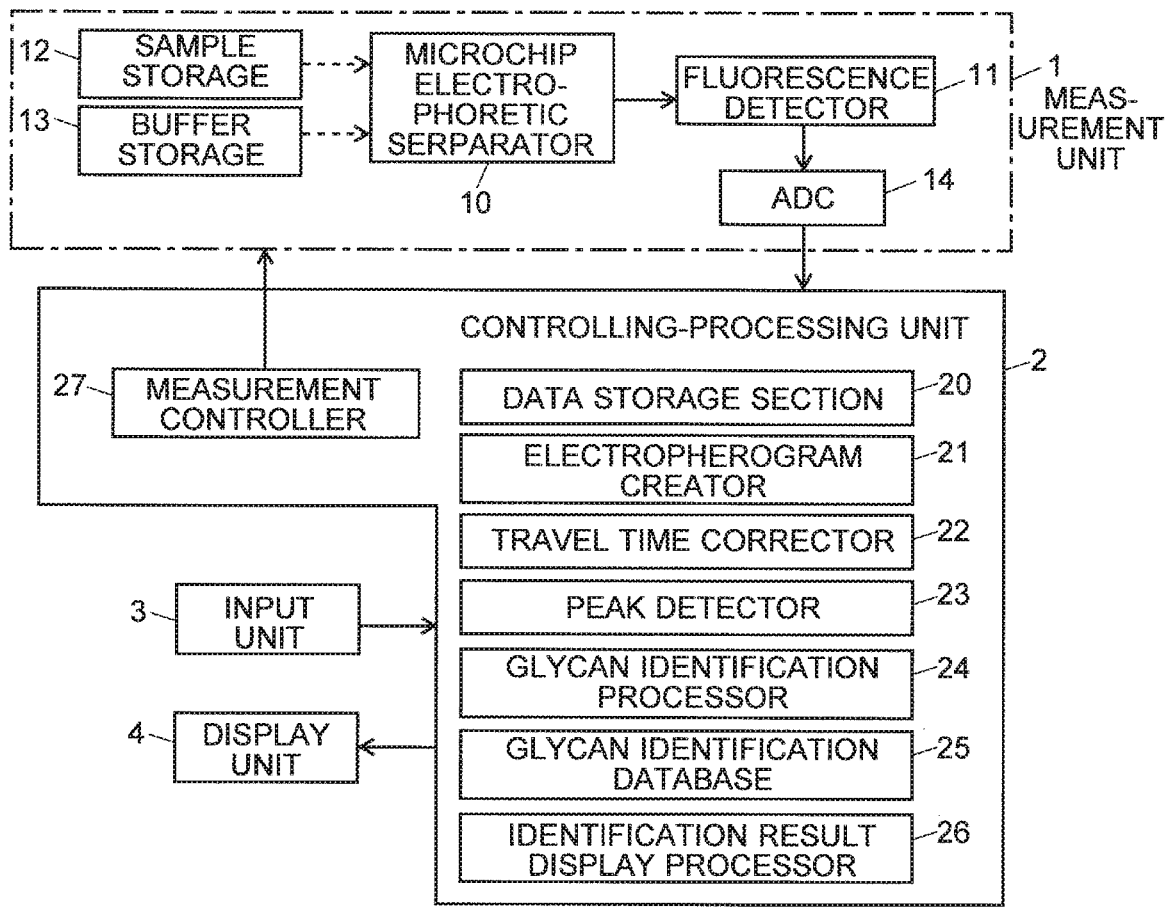
FIG. 2 is a schematic block diagram showing the configuration of one embodiment of the glycan analysis system according to the present invention.
Figure 3:
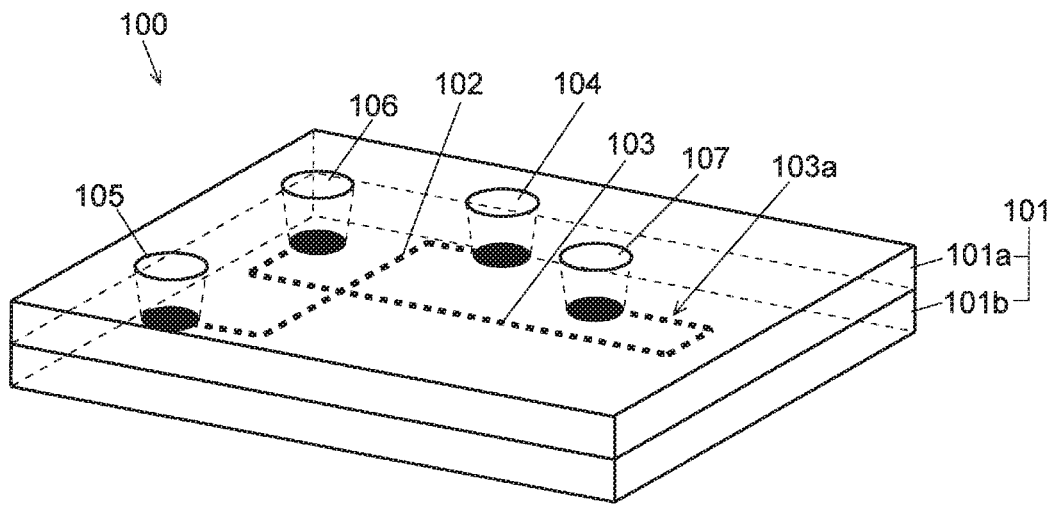
FIG. 3 is a schematic perspective view of a microchip for electrophoresis included in a microchip electrophoretic separator in the glycan analysis system according to the embodiment shown in FIG. 2.

One embodiment of the glycan analysis system for carrying out the glycan analysis method according to the present invention is hereinafter described. FIG. 2 is a schematic block diagram showing the configuration of the glycan analysis system according to the present embodiment. FIG. 3 is a schematic perspective view of a microchip for electrophoresis included in a microchip electrophoretic separator in the present glycan analysis system.

As shown in FIG. 2, the glycan analysis system according to the present embodiment includes a measurement unit 1, controlling-processing unit 2, input unit 3 and display unit 4. The measurement unit 1 includes a microchip electrophoretic separator 10, fluorescence detector 11, sample storage section 12, buffer storage section 13, analog-to-digital converter (ADC) 14 and other components.

Though not shown, the microchip electrophoretic separator 10 includes the following sections in addition to an electrophoresis chip (which will be described later): a pressurizing-suctioning section for filling the channel in the electrophoresis chip with a buffer solution prepared in the buffer storage section 13; a sample-dispensing section for dispensing a fraction of a sample prepared in the sample storage section 12 into the electrophoresis chip; a voltage-applying section for applying a voltage for electrophoretic migration and other voltages to the electrodes in the electrophoresis chip; and a washing section for washing the electrophoresis chip after the completion of a measurement. For example, the microchip electrophoresis device MCE-202 manufactured by Shimadzu Corporation, which is disclosed in Non-Patent Literature 3, can be used as the measurement unit 1. The microchip electrophoresis device MCE-202 can be loaded with a maximum of four electrophoresis chips and simultaneously carry out measurements in parallel using the four electrophoresis chips.

The controlling-processing unit 2 includes a data storage section 20, electropherogram creator 21, travel time corrector 22, peak detector 23, glycan identification processor 24, glycan identification database 25, identification result display processor 26, measurement controller 27 and other functional blocks. The glycan identification database 25 is a database holding a collection of information which shows, for each of the various known kinds of glycans and for each of the various kinds of lectins, whether or not the glycan has an affinity for the lectin, i.e. whether or not the lectin specifically binds to the glycan. FIG. 5 shows one example of the contents of the information in the glycan identification database 25.

Typically, in the glycan analysis system according to the present embodiment, the controlling-processing unit 2, input unit 3 and display unit 4 are actually a general-purpose personal computer (PC), with the functions of the aforementioned functional blocks fulfilled by executing, on this PC, dedicated controlling-processing software installed on the same PC. This controlling-processing software corresponds to the program for glycan analysis according to the present invention. The glycan identification database 25 may also be prepared by the vendor of the system and provided to users as a part of a glycan analysis tool along with a control program for controlling the application of the migration voltage.

FIG. 3 is a schematic perspective view of one example of an electrophoresis chip to be used in a microchip electrophoresis device. As shown in FIG. 3, the electrophoresis chip 100 includes a substrate 101 formed by a pair of transparent plates 101a and 101b made of quartz or a similar material shaped like a rectangular plate with each side measuring approximately one dozen millimeters to tens of millimeters in length. The lower transparent plate 101b has two mutually intersecting grooves formed on its upper surface. The upper transparent plate 101a has four through-holes each of which is formed at a position corresponding to one of the end portions of the two grooves. The two transparent plates 101a and 101b are bonded together to form a single body, with the grooves located inside the substrate 101 to form a sample introduction channel 102 communicating with the outside through the first reservoir 104 and the second reservoir 105 formed by two of the through-holes as well as a separation channel 103 communicating with the outside through the third reservoir 106 and the fourth reservoir 107 formed by the other two through-holes. Each of the reservoirs 104-107 has an extremely small capacity of one to several μL. An electrode (not shown) for applying a voltage to the migration solution (buffer solution for separation) stored in the reservoir is provided in each reservoir.

In this electrophoresis chip 100, an area 103*a* close to the fourth reservoir 107 in the separation channel 103 is the detection position. At this detection position, the fluorescence detector 11, which includes an excitation optical system for delivering excitation light into the separation channel 103 and a detection optical system for detecting fluorescent light emitted from the separation channel 103 due to the excitation light, is to be placed.

[Procedure of Glycan Identification and Contents of Processing]

The procedure for identifying glycans using the previously described glycan analysis system and the operations of the relevant sections in the system will be hereinafter described. FIG. 1 is a flowchart showing the procedure and the processing operations. For the following descriptions, it is assumed that the glycans to be analyzed are in the form of glycoproteins in which those glycans are linked to proteins.

An operator initially performs an operation for releasing glycans from glycopeptides to obtain a glycan mixture (Step S1). A conventional and common method can be used for this operation. Subsequently, the operator fluorescently labels the released glycans with a specific fluorescent reagent. There is no specific limitation on the kind of compound to be used for the fluorescent labeling. In the present example, 8-aminopyrene-1,3,6-trisulfonic acid (APTS) is used, which has also been used in the CAE method. By purifying the fluorescently-labeled glycans by the solid-phase extraction method employing size exclusion chromatography and normal-phase partition, a glycan mixture that can be used as a sample for the analysis is obtained (Step S2).

Next, the operator sets the fluorescently-labeled glycan mixture as a sample in the sample storage section 12 of the measurement unit 1. Meanwhile, the operator prepares, in the buffer storage section 13, a plurality of kinds of buffer solutions (lectin-added buffer solutions), to each of which one of the various kinds of previously selected lectins is added at a predetermined concentration, as well as a buffer solution with no lectin added (in the following descriptions, the original buffer solution before the addition of the lectin is simply called the "buffer solution", while the buffer solutions prepared in the buffer storage section 13 are called the "buffer solutions for separation", regardless of the addition or non-addition of the lectin). A reagent kit including a plurality of kinds of lectins can be used for this preparation task. This kit corresponds to the kit for glycan analysis according to the present invention.

Then, the operator performs a predetermined operation on the input unit 3. In response to this operation, the measurement controller 27 operates the measurement unit 1 according to a previously determined program to perform a measurement by the microchip electrophoretic separator 10 and the fluorescence detector 11, using each of the buffer solutions for separation including the no-lectin buffer solution (Step S3). As will be described later in detail, a high-concentration separating gel is used as the buffer solution. This separation gel is obtained by mixing an appropriate kind of neutral polymer into a common liquid buffer at an appropriate concentration.

Under the control of the measurement controller 27, one measurement for a sample is performed as follows: The channels 102 and 103 in the electrophoresis chip 100 which has been washed are filled with one of the plurality of kinds of buffer solutions for separation prepared in the buffer storage section 13. A predetermined amount of sample prepared in the sample storage section 12 is subsequently collected and dispensed into the first reservoir 104. Then, a predetermined amount of voltage is applied between the electrode of the first reservoir 104 and that of the second reservoir 105. Due to the electric field created within the sample introduction channel 102 by this voltage, the sample in the first reservoir 104 migrates toward the second reservoir 105. If the buffer solution for separation contains a lectin, the lectin binds to a specific kind of glycan in the sample according to its carbohydrate-binding specificity.

After the passage of a predetermined period of time, the application of the voltage to the electrodes of the first reservoir 104 and that of the second reservoir 105 is discontinued, and a predetermined amount of migration voltage is subsequently applied to between the electrode of the third reservoir 106 and that of the fourth reservoir 107. This voltage creates a migration electric field within the separation channel 103. A trace amount of sample which has been present at the intersection of the sample introduction channel 102 and the separation channel 103 immediately before the creation of this electric field within the separation channel 103 is made to migrate toward the fourth reservoir 107 due to the effect of this electric field. In the course of the migration, the glycans in the sample are separated from each other according to their mass-to-charge ratios and other properties. Since the buffer solution for separation is a high-concentration separating gel, a molecular-sieving effect works, so that the separation by molecular weight is more effectively achieved. As noted earlier, a glycan with a lectin attached has a larger mass and a lower migration speed than the same glycan with no lectin attached. The fluorescence detector 11 sequentially detects each of the individual glycans which have been thus separated, and produces a detection signal corresponding to the intensity of the fluorescent emission from the APTS attached to the glycan. This detection signal is converted into a digital form by the ADC 14 and temporarily stored in the data storage section 20 of the controlling-processing unit 2.

After the passage of a predetermined length of measurement time from the beginning of the application of the migration voltage, the application of the voltage is discontinued, and the channels 102 and 103 are washed in a predetermined manner. Thus, one measurement cycle is completed. Such a measurement cycle is repeated for each of the previously specified kinds of buffer solutions for separation to collect measurement data for one sample under the plurality of kinds of buffer solutions for separation.

After the completion of the entire measurement, the electropherogram creator 21 in the controlling-processing unit 2 creates an electropherogram showing a relationship between travel time and fluorescent intensity based on the data stored in the data storage section 20 (Step S4). In this step, the travel time may be corrected as follows:

A reference substance which binds to none of the lectins (and undergoes no change in travel time), and which overlaps with none of the glycans in travel time, is added to the sample beforehand. In the measurement of the sample, this reference substance is detected along with the glycans. It is preferable to use two reference substances, one of which is guaranteed to have a shorter travel time than any of the glycans concerned under the no-lectin buffer solution while the other substance is guaranteed to have a longer travel time. The travel time of the reference substance should always be the same in the plurality of electropherograms obtained for different buffer solutions for separation. Accordingly, the travel time corrector 22 detects a peak corresponding to the reference substance, and corrects the horizontal axis of the electropherogram. i.e. the travel times of the peaks which respectively correspond to the glycans, based on the travel time of that peak. As the reference substance, a glycan which does not interact with any of the used lectins can be used, such as an oligosaccharide of cellulose.

Next, the peak detector 23 and the glycan identification processor 24 identify glycans contained in the sample based on a plurality of electropherograms obtained with different kinds of lectins (Step S5).

Specifically, the peak detector 23 detects peaks on each of the electropherograms according to a predetermined algorithm. The glycan identification processor 24 compares each of the electropherograms obtained under the buffer solutions for separation, exclusive of the no-lectin buffer solution, with the electropherogram obtained under the no-lectin buffer solution, to determine whether or not each peak detected on the electropherogram obtained under the no-lectin buffer solution is present at the same travel time on the electropherogram being compared. Then, with reference to the glycan identification database 25, the glycan identification processor 24 determines the kinds of glycans corresponding to the peaks detected on the electropherogram obtained under the no-lectin buffer solution, based on the travel time of each peak and the information showing the presence/absence of the peak for each kind of lectin. The identification result display processor 26 displays the identified glycans on the display unit 4 (Step S6).

In a normal glycan analysis, the kind of living organism and the location of the biological tissue from which a glycan mixture being analyzed has been sampled is known beforehand. This fact considerably limits the kinds of glycans which may possibly be detected. Accordingly, the glycan identification processor 24 can narrow down the glycans recorded in the glycan identification database 25 to a smaller number of glycan candidates based on previously given information concerning the sample, and consider only those candidates in determining the assignment of each peak based on the affinity with each lectin.

The method for identifying glycans contained in a sample based on the obtained electropherograms is not limited to a method in which a database is searched for information that matches the presence/absence pattern of the peak in the previously described manner.

After each peak observed on the electropherogram obtained under the no-lectin buffer solution has been assigned, it is possible estimate the amount of glycan from the intensity (peak area or peak height) of the peak, and specifically, by referring to a previously created calibration curve. In other words, it is possible to quantitatively determine the identified glycan. In the previously described method, since the lectin is added to the buffer solution in sufficient quantity, the lectin binds to almost all glycans in the sample for which the lectin has a binding specificity, so that the peak corresponding to that glycan disappears (i.e. its travel time is delayed). As another possibility, the amount of lectin to be added to the buffer solution may be appropriately controlled to investigate the relationship between the added amount of lectin and the degree of decrease of the peak of the corresponding glycan (e.g. the degree of decrease in the area of the peak). This allows for the estimation of the magnitude of the affinity between the glycan concerned and a specific kind of lectin.

The method according to the present invention can also be used for distinguishing between isomers which have the same mass and different structures. In the example mentioned earlier, the $\alpha$2-6-linked N-acetylneuraminic acid residue to which SSA specifically binds, and the $\alpha$2-3-linked N-acetylneuraminic acid residue to which MAM specifically binds, have the same mass and cannot be separated from each other by normal electrophoresis. On the other hand, the results shown in FIGS. 8A-8D demonstrate that the sialoglycan derived from human fibrinogen has a linkage type which includes the $\alpha$2-6-linked N-acetylneuraminic acid residue but does not include the $\alpha$2-3-linked N-acetylneuraminic acid residue. This means that the two isomers have been successfully distinguished.

As another example, UEA-I mainly has a binding specificity for a fucose residue which is $\alpha$-2,3-linked to galactose. AAL mainly has a binding specificity for a fucose residue which is $\alpha$-1,2-linked, $\alpha$-1,3-linked, $\alpha$-1,4-linked, or $\alpha$-1,6-linked to N-acetylglucosamine. AOL (*Aspergillus oryzae* Lectin) mainly has a binding specificity for a fucose residue which is $\alpha$-1,6-linked to N-acetylglucosamine. Accordingly, it is possible to distinguish between different linkage types of fucose by combining those three kinds of lectins.

Thus, isomers which cannot be separated from each other by normal electrophoresis can also be distinguished by selecting appropriate kinds of lectins to be used.

It should be noted that the previous embodiments are mere examples of the present invention, and any change, modification, addition or the like appropriately made within the spirit of the present invention will naturally fall within the scope of claims of the present application.

REFERENCE SIGNS LIST

1 . . . Measurement Unit
10 . . . Electrophoretic Separator
100 . . . Electrophoresis Chip
101 . . . Substrate
101a, 101b . . . Transparent Plate
102 . . . Sample Introduction Channel
103 . . . Separation Channel
104-107 . . . Reservoir
11 . . . Fluorescence Detector
12 . . . Sample Storage Section
13 . . . Buffer Storage Section
2 . . . Controlling-Processing Unit
20 . . . Data Storage Section
21 . . . Electropherogram Creator
22 . . . Travel Time Corrector
23 . . . Peak Detector
24 . . . Glycan Identification Processor
25 . . . Glycan Identification Database
26 . . . Identification Result Display Processor
27 . . . Measurement Controller
3 . . . Input Unit
4 . . . Display Unit

The invention claimed is:
1. A glycan analysis method, comprising:
a) a fluorescent-labeling step in which a glycan in a sample is fluorescently labeled;
b) a measurement step in which a sample containing a fluorescently-labeled glycan is separated by a microchip electrophoretic method using at least two kinds of buffer solutions for separation selected from a simple buffer solution with no lectin added and a plurality of kinds of lectin-added buffer solutions each of which contains a different kind of lectin added to the simple buffer solution, and the sample is fluorescently detected; and c) an identification step in which the glycan in the sample is identified by comparing a plurality of electropherograms obtained by a measurement using the at least two kinds of different buffer solutions for separation, wherein separation conditions in the microchip electrophoresis method including a kind of simple buffer solution are such conditions under which glycans having different degrees of polymerization ranging from monosaccharide to icosasaccharide can be separated from each other in a measurement of an isomalto-oligosaccharide mixture, and wherein DSA (*Datura stramonium* Agglutinin) is used as the lectin.

2. The glycan analysis method according to claim 1, wherein:

the simple buffer solution is a separating gel having a concentration which produces a molecular-sieving effect.

3. The glycan analysis method according to claim 1, wherein:

the simple buffer solution is a separating gel having a concentration which makes electrophoretic migration of proteins ignorable.

4. The glycan analysis method according to claim 1, wherein:

the simple buffer solution is a buffer solution which has no interaction with the lectin in the lectin-added buffer solution.

5. The glycan analysis method according to claim 1, wherein:

the simple buffer solution is a buffer solution which undergoes no change in pH due to addition of a lectin.

6. The glycan analysis method according to claim 1, wherein:

separation conditions in the microchip electrophoresis method including a kind of simple buffer solution are such conditions under which addition or non-addition of a lectin to the simple buffer solution causes no change in migration time of a glycan for which the lectin has no specificity.

7. A system for carrying out the glycan analysis method according to claim 1, comprising:

a) a measurement unit including a microchip electrophoresis section for separating components in a sample and a detection section for fluorescently detecting the components separated by the microchip electrophoresis section;

b) a glycan identification database recording, for known kinds of glycans, information concerning a plurality of electropherograms to be obtained by a measurement using at least two kinds of different buffer solutions for separation selected from a simple buffer solution with no lectin added and a plurality of kinds of lectin-added buffer solutions, or information concerning a peak to be observed on the plurality of electropherograms;

c) a peak detector configured to detect a peak on electropherograms individually obtained by a measurement performed on a sample containing an unknown fluorescently-labeled glycan using the measurement unit under each of the at least two kinds of buffer solutions for separation; and d) an identification processor configured to identify the glycan in the sample based on a result of a peak detection by the peak detector and the information recorded in the glycan identification database.

8. A non-transitory computer readable medium recording a program for glycan analysis to be installed on a computer to carry out the glycan analysis method according to claim 1, the program configured to make the computer function as:

a) a measurement-controlling functional section configured to control an operation of a measurement unit including a microchip electrophoresis section and a detection section, so as to separate a sample containing a fluorescently-labeled glycan by a microchip electrophoretic method using at least two kinds of buffer solutions for separation selected from a simple buffer solution with no lectin added and a plurality of kinds of lectin-added buffer solutions respectively prepared by adding a plurality of kinds of lectins to the simple buffer solution, and to fluorescently detect the sample; and b) an identification processing functional section configured to create a plurality of electropherograms each of which is based on data obtained by a measurement using one of the at least two kinds of different buffer solutions for separation under a control of the measurement-controlling functional section, and to identify the glycan in the sample by comparing the plurality of electropherograms.

9. A kit for glycan analysis to be used for carrying out the glycan analysis method according to claim 1, comprising:

a plurality of kinds of lectins to be added as buffer solutions for separation.

* * * * *